US009678039B2

(12) United States Patent
Sharp et al.

(10) Patent No.: US 9,678,039 B2
(45) Date of Patent: Jun. 13, 2017

(54) ION MODIFICATION

(71) Applicants: David Sharp, Hertfordshire (GB);
Jonathan Atkinson, Hertfordshire (GB)

(72) Inventors: David Sharp, Hertfordshire (GB);
Jonathan Atkinson, Hertfordshire (GB)

(73) Assignee: Smiths Detection-Watford Limited,
Hertfordshire (GB)

( * ) Notice: Subject to any disclaimer, the term of this patent is extended or adjusted under 35 U.S.C. 154(b) by 0 days.

(21) Appl. No.: 14/776,938

(22) PCT Filed: Mar. 12, 2014

(86) PCT No.: PCT/GB2014/050744
§ 371 (c)(1),
(2) Date: Sep. 15, 2015

(87) PCT Pub. No.: WO2014/140577
PCT Pub. Date: Sep. 18, 2014

(65) Prior Publication Data
US 2016/0054263 A1    Feb. 25, 2016

(30) Foreign Application Priority Data
Mar. 15, 2013  (GB) .................................. 1304776.6

(51) Int. Cl.
*G01N 27/62* (2006.01)
*H01J 49/00* (2006.01)
*H01J 49/40* (2006.01)

(52) U.S. Cl.
CPC ........ *G01N 27/622* (2013.01); *H01J 49/0027* (2013.01); *H01J 49/40* (2013.01)

(58) Field of Classification Search
USPC .......................... 250/281, 282, 286, 287, 288
See application file for complete search history.

(56) References Cited

U.S. PATENT DOCUMENTS

| 2005/0173629 A1 | 8/2005 | Miller et al. |
| 2009/0039248 A1 | 2/2009 | Atkinson et al. |
| 2010/0108877 A1 | 5/2010 | Ching et al. |
| 2010/0127166 A1 | 5/2010 | Krueger et al. |

FOREIGN PATENT DOCUMENTS

| WO | 2006114580 | 11/2006 |
| WO | 2014140577 | 9/2014 |

OTHER PUBLICATIONS

PCT/GB2014/050744 Search Report dated Jun. 24, 2014.
GB1304776.6 Search Report dated Oct. 7, 2013.

*Primary Examiner* — Nicole Ippolito
*Assistant Examiner* — Hanway Chang
(74) *Attorney, Agent, or Firm* — Advent, LLP

(57) ABSTRACT

An ion mobility spectrometry method comprising determining whether a sample comprises ions having a first characteristic, and in the event that it is determined that the sample comprises ions having the first characteristic, applying thermal energy together with a radio frequency, RF, electric field to parent ions so as to obtain daughter ions having a second characteristic for inferring at least one identity for the parent ions based on the first characteristic and the second characteristic.

18 Claims, 4 Drawing Sheets

ION MODIFICATION

The present disclosure relates to apparatus and methods, and more particularly to spectrometers, and to spectrometry methods.

Ion mobility spectrometers (IMS) can identify material from a sample of interest by ionizing the material (e.g., molecules, atoms, and so forth) and measuring the time it takes the resulting ions to travel a known distance under a known electric field. An ion's time of flight can be measured by a detector, and the time of flight is associated with the ion's mobility. An ion's mobility relates to its mass and geometry. Therefore, by measuring the time of flight of an ion in the detector it is possible to infer an identity for the ion. These times of flight may be displayed graphically or numerically as a plasmagram.

In some instances, modifying some of the ions using a radio frequency, RF, electric field (e.g. by fragmenting them) to provide additional information can be used to infer an identity for the ions. This provides additional degrees of freedom in the measurement of the ions, and therefore may improve the ability to resolve differences between ions that may be difficult to differentiate. Where measurements are performed in the presence of contaminants, or in difficult operating conditions, or where a sample comprises ions with similar geometries and masses etc. the IMS's ability to detect and identify ions, and ion modification is one way to address these issues.

Embodiments of the disclosure will now be described, by way of example only, with reference to the accompanying drawings, in which.

Embodiments of the disclosure relate to the selective application of thermal energy in combination with an alternating, e.g. RF, electric field to modify ions from a sample of interest. This may enable less energy to be used to modify ions than may be needed when an electric field or thermal energy are used alone. This may enable portable spectrometry apparatus, such as hand held and/or battery powered apparatus, to be operated with improved efficiency.

An ion mobility spectrometer can determine whether a sample comprises ions having a first characteristic, for example a time of flight associated with one or more substances of interest. The ion mobility spectrometer can then be operated to apply thermal energy together with a radio frequency, RF, electric field to parent ions so as to obtain daughter ions. The daughter ions may then have a second characteristic (for example, a second time of flight), and this may enable an identity, or a selection of candidate identities, to be determined for the parent ions based on the first characteristic and the second characteristic.

As another example of the disclosure, an ion mobility spectrometer can comprise an ion modifier configured to apply an RF electric field to ions in a region of the spectrometer, e.g. a predefined region adjacent the ion modifier; a heater configured to heat the region; and a controller configured to operate the heater to heat the region prior to operating the ion modifier to apply the RF electric field. This heating may be localised so that the region is heated more than other regions of the spectrometer. For example, the ion modifier may be arranged to apply an RF electric field to ions in a region of a drift chamber of the spectrometer, and the heater may be configured to heat that region more than other regions of the drift chamber.

Figure 1:
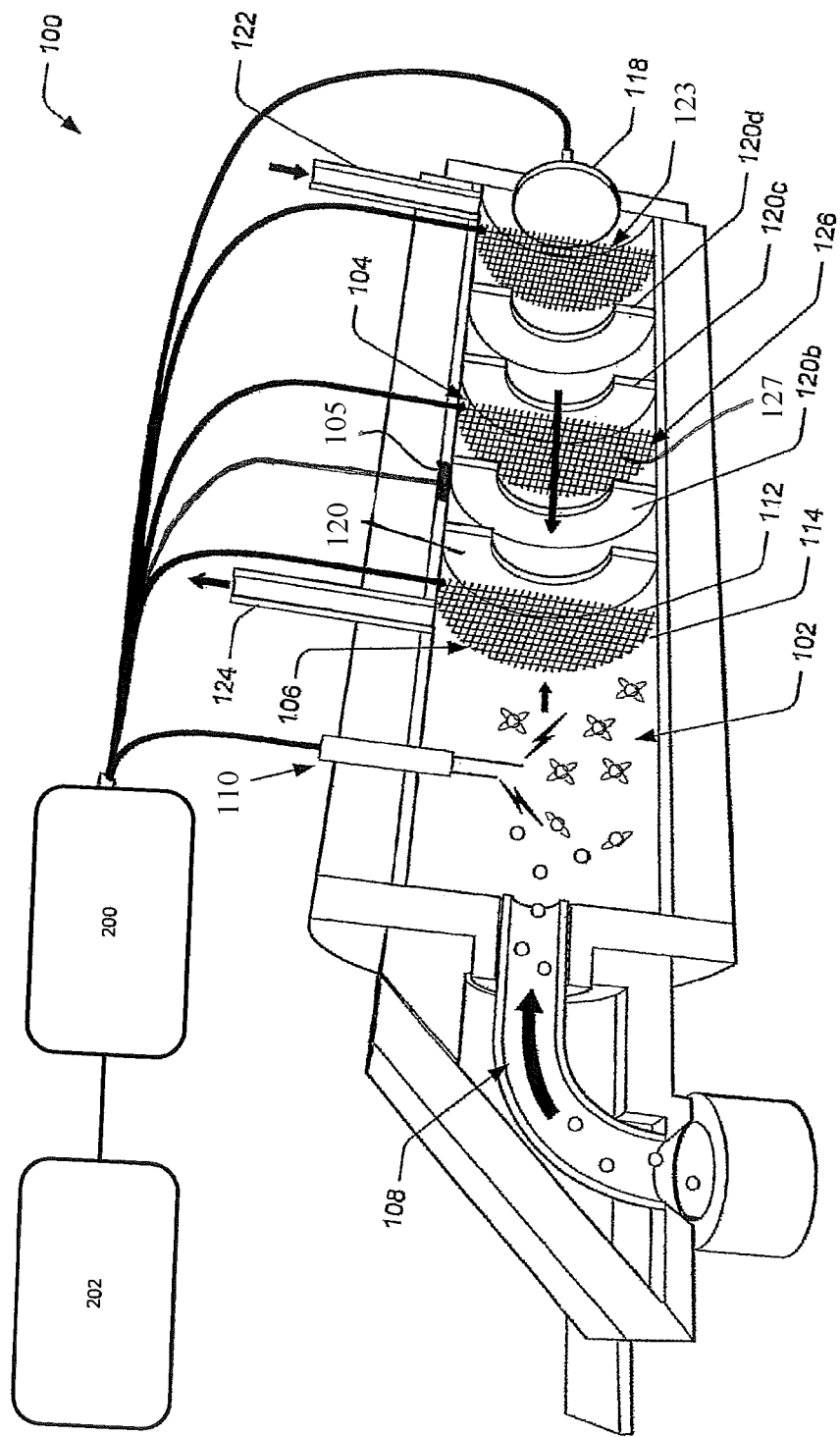
FIG. 1 is an illustration of a spectrometer.

FIG. 1 is an illustration of an ion mobility spectrometer (IMS) 100 which includes an ionisation chamber 102 that is separated from a drift chamber 104 by a gate 106. The gate 106 can control passage of ions from the ionisation chamber 102 into the drift chamber 104. In FIG. 1, an ionisation source 110 is arranged for ionising material in the ionisation chamber 102. As illustrated, the IMS 100 includes an inlet 108 for enabling material to be introduced from a sample of interest to the ionisation chamber 102.

In the example illustrated in FIG. 1, the drift chamber 104 lies between the ionisation chamber 102 and a detector 118, so that ions can reach the detector 118 by traversing the drift chamber. The drift chamber 104 may comprise a series of electrodes 120a-d for applying an electric field in the drift chamber to move ions from the ionisation chamber along the drift chamber 104 toward the detector 118.

The IMS 100 may be configured to provide a flow of drift gas in a direction generally opposite an ion's path of travel to the detector 118. For example, the drift gas can flow from adjacent the detector 118 toward the gate 106. As illustrated, a drift gas inlet 122 and drift gas outlet 124 can be used to pass drift gas through the drift chamber. Example drift gases include, but are not limited to, nitrogen, helium, air, air that is re-circulated (e.g., air that is cleaned and/or dried) and so forth.

The detector 118 may be coupled to provide a signal to a characteristic determiner 200. Current flow from the detector 118 can be used by the characteristic determiner 200 to infer that ions have reached the detector 118, and a characteristic of the ions can be determined based on the time for ions to pass from the gate 106 along the drift chamber 104 to the detector 118. Examples of a detector 118 are configured to provide a signal indicating that ions have arrived at the detector 118. For example, the detector may comprise a faraday plate, which may be charged to catch ions.

Electrodes 120a-d may be arranged to guide ions toward the detector 118, for example the electrodes 120a-d may comprise rings which may be arranged around the drift chamber 104 to focus ions onto the detector 118. Although the example of FIG. 1 includes a plurality of electrodes 120a-d, in some examples only two electrodes may be used, or a single electrode may be used in combination with the detector 118 to apply an electric field to guide ions toward the detector 118. Other electrode configurations are also possible, examples include, but are not limited to electrodes of other geometric shapes and electrically resistive and/or conductive (e.g., a resistive electrical conductor) coatings, such as a continuous coating.

A radio frequency, RF, electrode 126 can be arranged across the drift chamber 104 such that ions passing from the ionisation chamber to the detector pass the RF electrode. The RF electrode may comprise a grid of conductors, which may comprise a metal such as nickel. In one example, the conductors may be 20 microns in diameter. In one example these conductors may be spaced 30 microns apart. The RF electrode may comprise two electrodes, for example two grids, which may be spaced apart. In one example the spacing between the two grids may be 250 microns. The RF electrode may subject ions in a region of the drift chamber 104 to an RF electric field. Where the RF electrode 126 comprises two electrodes, the region may be provided by the spacing between the electrodes.

In FIG. 1 the RF electrode 126 comprises a heater 127 arranged for providing thermal energy to the region of the drift chamber in which the RF electrode 126 is arranged to subject ions to an RF electric field. In the example of FIG. 1, the heater 127 comprises a resistive electrical conductor, which may be a part of the RF electrode 126.

In the example illustrated in FIG. 1, the characteristic determiner 200 is coupled to a controller 202, and the controller can be configured to selectively control the application of an RF voltage to the RF electrode 126; and heating by the heater 127. Accordingly, the controller 202 can control the application of thermal energy and/or an RF electric field, based on a characteristic of ions determined by the characteristic determiner 200.

The spectrometer 100 may comprise a guard 123 which may comprise a conductor arranged to provide an equipotential screen to inhibit the electric field associated with an ion reaching the detector before the ion actually arrives at the detector. This may inhibit the detector from falsely detecting the arrival of an ion before it reaches the detector 118. The guard 123 may be provided by a conductive material, which may be arranged in a grid. The guard 123 may be coupled to a selected voltage, for example by the controller 202.

The spectrometer 100 may comprise a sensor 105 for sensing the temperature in the drift chamber 104 and for providing a signal based on the sensed temperature to the controller 202. The sensor 105 may be disposed in the drift chamber 104, for example the sensor 105 may be carried by a wall of the drift chamber. The temperature sensor 105 may comprise any sensor, such as an electrical sensor (for example an electronic sensor) which may comprise a thermistor or a thermocouple. The controller 202 may be configured to obtain a signal from the temperature sensor 105, and to enable operation of the heater 127 to apply thermal energy in the event that the temperature is less than a selected threshold temperature. For example the controller 202 may be configured so that the heater 127 is not operated unless the temperature is less than a selected threshold temperature.

In operation of the spectrometer 100, material from a sample can be introduced into the ionisation chamber 104 via the inlet 108 where it can be ionised by the ionisation source 110. The controller 202 can then operate the gate 106 to introduce ions into the drift chamber 104 so the characteristic determiner 202 can determine a characteristic of the ions (e.g. based on their time of flight in the drift chamber 104).

The controller 202 may be configured so that, in the event that the characteristic determiner 200 determines that ions from a sample have a selected characteristic, such as a time of flight associated with a substance of interest, a determination can be performed to infer an identity for the ions. This may comprise obtaining further ions from the sample, and operating the gate 106 to introduce these ions into the drift chamber 104. The controller 202 can then operate either the RF electrode 126 or the heater 127 to modify the ions, for example by fragmenting them and then determining a first characteristic of those ions, e.g. a time of flight of those ions.

The controller can also be configured so in the event that the first characteristic of the modified ions comprises a selected characteristic, such as a time of flight associated with a substance of interest, the RF electric field and thermal energy can be applied together to modify ions from the sample to determine a second characteristic, which may be a subsequent measurement of the same property of these modified ions, for example the time of flight associated with the modified ions.

Applying thermal energy together with the RF electric field may comprise the controller 202 being configured to operate the heater 127 to apply thermal energy for a selected period prior to operating the gate 106 to introduce ions into the drift chamber. In embodiments the controller may be configured to apply thermal energy together with the RF electric field by operating the gate 106 to introduce ions into the drift chamber 104, and then operating the heater 127 to apply thermal energy to a region around the RF electrode.

In FIG. 1 the RF electrode 126 comprises the heater 127. For example, one or more conductors of the RF electrode 127 may be coupled to receive an electric current for ohmic heating of the electrode, this may comprise a current provided in addition to an RF voltage used to apply the RF electric field, for example a DC current may be passed through one or more conductors of the RF electrode to provide heating.

The RF electrode 126 may not comprise the heater 127. In addition, or as an alternative, the heater may comprise a grid of conductors, which may be arranged across the drift chamber. In embodiments where the RF electrode 126 comprises a grid, the pitch of the heater grid (e.g. the spacing between adjacent conductors) may be selected based on the pitch of the RF electrode 126. For example the pitch of conductors in the heater 127 may be the same as the pitch of conductors of the RF electrode 126, or the pitch of the conductors of the RF electrode 126 may be an integer multiple of the pitch of the conductors in the heater, or vice versa. In these examples the arrangement of the conductors of the heater 127 and the RF electrode 126 may be arranged to correspond, for example so a cross section of the drift chamber along which ions can pass is not reduced by the presence of the heater. A grid of conductors may include straight conductors arranged in parallel, for example the conductors may be arranged in a lattice so that they cross one another, or the conductors of a grid may be arranged so they do not cross.

Where the RF electrode 126 does not comprise the heater 127, the heater 127 may be arranged so that electrical interaction (e.g. capacitive and/or inductive) coupling between the heater 127 and the RF electrode 126 does not prevent the RF electrode 126 from modifying ions.

The heater 127 may be spaced from the RF electrode 126 a distance selected so the heater 127 does not prevent the RF electrode 126 from modifying ions. Additionally, or as an alternative, the geometry and/or orientation of the heater relative to the RF electrode may be selected so it does not prevent the RF electrode 126 from modifying ions. Additionally, or as an alternative, the electric potential of the heater 127 may be selected based on the electric potential of the RF electrode 126 so that the presence of the heater 127 does not prevent the RF electrode 126 from modifying ions. In some examples the heater 127 is arranged with respect to the RF electrode 126 so as to inhibit capacitive and/or inductive coupling between the heater 127 and the RF electrode 126. In some examples the voltage and/or impedance of the heater 12 are selected to inhibit capacitive and/or inductive coupling between the heater 127 and the RF electrode 126.

The heater 127 may be arranged between the drift gas inlet 122 and the RF electrode 126, for example the guard 123 may comprise the heater 127. The heater may be arranged between the RF electrode 126 and the drift gas outlet 124, for example the gate 106 may comprise the heater. In embodiments the electrodes 120a, 120b, 120c may comprise the heater. The heater may be arranged at the drift gas inlet 122 to heat the drift gas on or prior to entry into the drift chamber 104. The heater 127 may comprise a radiative heat source, such as an source of infra-red radiation, for example a laser which may be arranged to direct thermal energy to a region of the drift chamber to which the RF electrode is adapted to apply an RF electric field.

Applying thermal energy may comprise heating the region around the RF electrode to a temperature that is insufficient to modify ions without the application of an RF electric field. For example, applying thermal energy may comprise heating the region to a temperature of at least 30° C., for example at least 35° C., for example at least 40° C. and/or to a temperature of less than 120° C., for example less than 100° C. The controller 202 may be configured to control the heater 127 based on a signal from the temperature sensor.

The characteristic determiner 200 may comprise a timer, and the characteristic determiner may be coupled to determine the time between the ions being introduced to the drift chamber, and one or more ions being detected by the detector 118. The timing of the ions being introduced to the drift chamber may be determined based on operation of the gate 106.

The characteristic determiner may comprise a look up table to enable characteristics of ions to be determined based on this timing. The determined characteristic of the ions may comprise one or more characteristics selected from the list comprising: the time of flight of ions, the charge of the ions, the mass of the ions, a mobility of the ions, and the mass/charge ratio of the ions. For example the time of flight may be the time between the ions being introduced to the drift chamber 104 and their arrival at the detector, for example the time between operating the gate 106 to allow ions into the drift chamber 104 and their arrival at the detector 118.

The controller 202, and/or the characteristic determiner 200 may be provided by any appropriate controller, for example by analogue and/or digital logic, field programmable gate arrays, FPGA, application specific integrated circuits, ASIC, a digital signal processor, DSP, or by software loaded into a programmable general purpose processor.

FIGS. 2A to 2E are schematic diagrams of examples of spectrometers to illustrate variations of the spectrometer illustrated in FIG. 1.

In FIG. 1 and FIGS. 2A to 2E like reference numerals are used to indicate like elements.

Figure 2A:
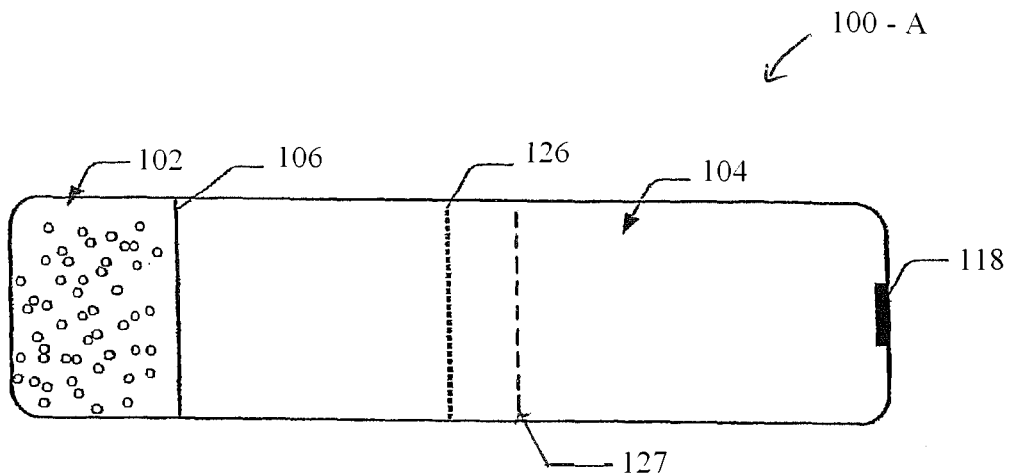
FIGS. 2A to 2E are schematic diagrams of examples of spectrometers to illustrate variations of the spectrometer illustrated in FIG. 1.

FIG. 2A illustrates a spectrometer 100-A which comprises a heater 127 disposed in the drift chamber 104 between the detector 118 and the RF electrode 126. The heater 127 may comprise a resistive heater, such as a grid of conductors arranged across the drift chamber.

Figure 2B:
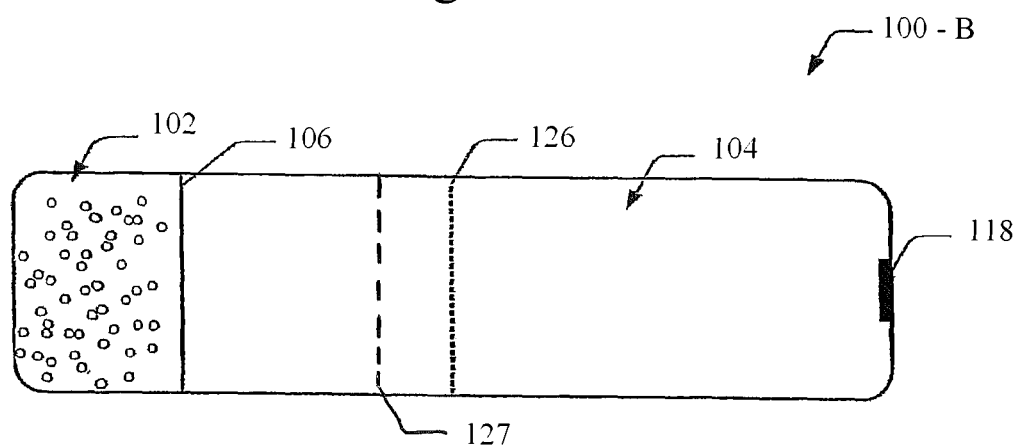

FIG. 2B illustrates a spectrometer 100-B which comprises a heater 127 disposed in the drift chamber 104 between the ionisation chamber 102 and the RF electrode 126. The heater 127 may comprise a resistive heater, such as a grid of conductors arranged across the drift chamber.

Figure 2C:
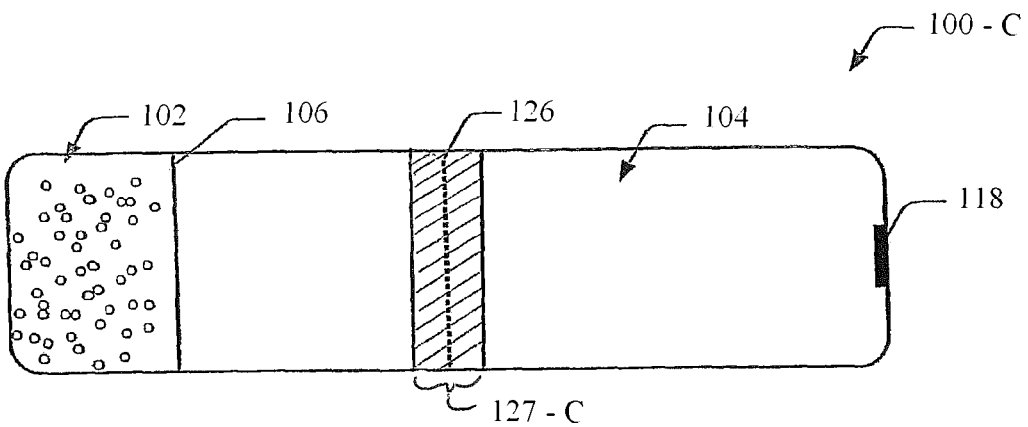

FIG. 2C illustrates a spectrometer 100-C which comprises a heater 127-C disposed around the drift chamber 104 carried by a wall of the drift chamber 104. The heater 127-C may comprise a film heater for example comprising a resistive film or tape for heating the region of the drift chamber 104 around the RF electrode 126.

Figure 2D:
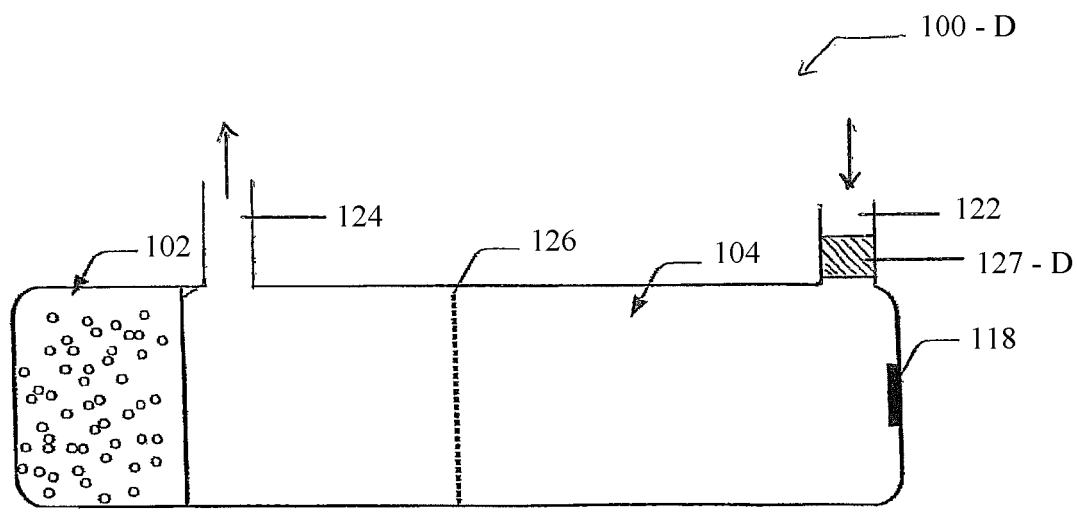

FIG. 2D illustrates a spectrometer 100-D which comprises a heater 127-D disposed at the drift gas inlet 122 for heating the drift gas flowing into the drift chamber 104. The heater 127-E of FIG. 2E may be disposed in and/or around the drift gas inlet, for example it may comprise a resistive film, coating or tape carried by a wall of the drift gas inlet 122. In addition, or as an alternative, the heater 127-D of FIG. 2D may comprise a grid of conductors arranged across the drift gas inlet.

Figure 2E:
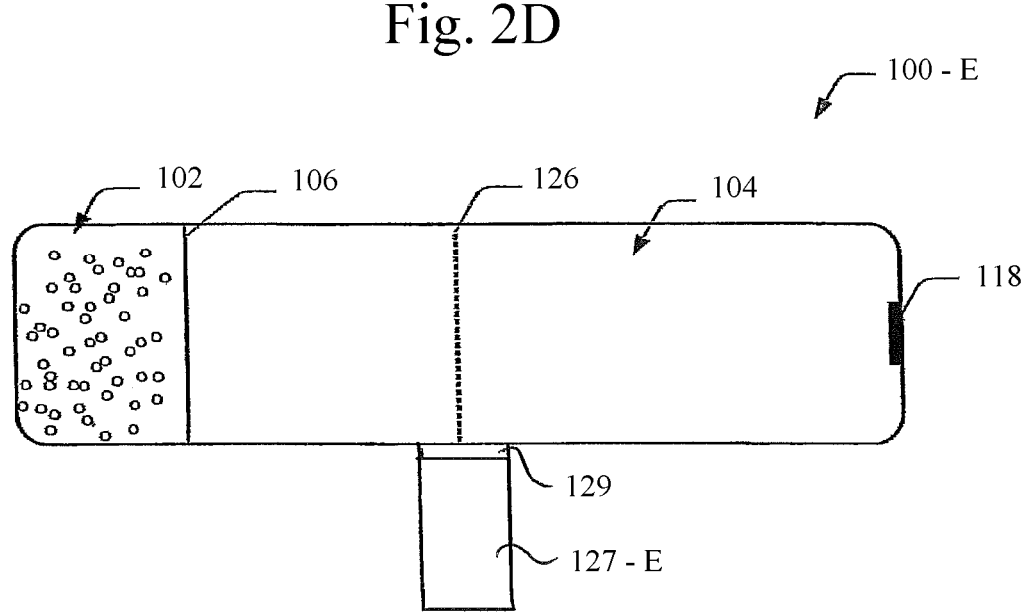

FIG. 2E illustrates a spectrometer 100-E in which a transmissive window 129 may be provided in a wall of the drift chamber 104 to enable a radiative heat source 127-E to radiate thermal energy into a region of the drift chamber comprising the RF electrode 126.

Figure 3:
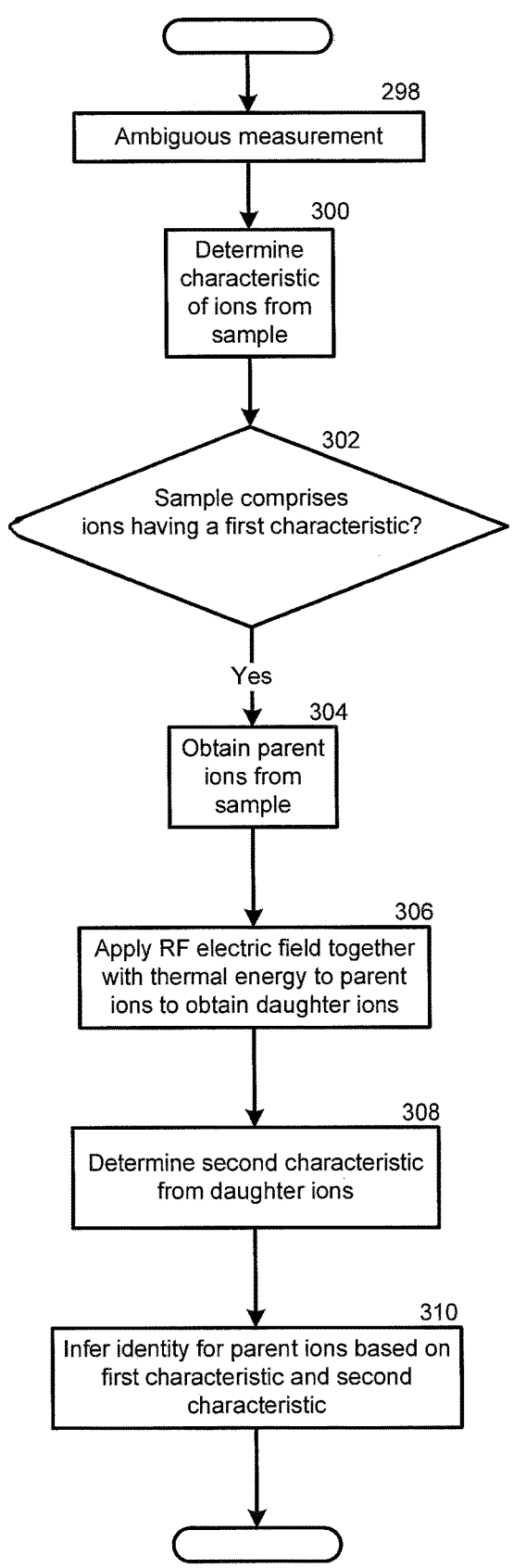
FIG. 3 is a flow diagram illustrating a method of operating a spectrometer.

FIG. 3 illustrates a method in which a spectrometry measurement may be performed. In the event that the spectrometry measurement provides an ambiguous result 298, the method may comprise performing a further determination to resolve the ambiguous result. In this case, the method comprises determining 300 whether a sample comprises ions having a first characteristic, e.g. a selected time of flight. In the event that it is determined that the sample does 302 comprise ions having the first characteristic, the method may comprise obtaining 304 ions from the sample and applying 306 energy to modify the ions so as to obtain daughter ions. Applying 306 energy may comprise applying a radio frequency, RF, electric field, or applying thermal energy, or applying thermal energy together with a radio frequency, electric field to those ions so as to obtain daughter ions.

A second characteristic of the daughter ions can then be determined 308, e.g. the time of flight of the daughter ions. This may enable an identity to be inferred 310 for the parent ions based on the first characteristic and the second characteristic of the daughter ions. The first characteristic and the second characteristic may be subsequent measurements of the same parameter e.g. the time of flight.

In some embodiments, in the event that a spectrometery measurement performed without ion modification provides an ambiguous result 298, the method may comprise obtaining 304 ions from the sample and applying 306 a radio frequency, RF, electric field, or applying thermal energy, to modify the ions to obtain first daughter ions. A characteristic of the first daughter ions can then be determined 308, e.g. the time of flight of the first daughter ions.

To obtain further information, further ions can be obtained from the sample and an RF electric field can then be applied to the ions together with thermal energy, to modify the ions to obtain second daughter ions. A characteristic of these second daughter ions can then be determined 308, e.g. their time of flight. This may enable an identity to be inferred 310 for the parent ions based on the characteristic of the parent ions, and the characteristic of the first and second daughter ions.

In a first method example, a method comprises determining whether the sample comprises the ions having the first characteristic comprises applying an RF electric field and/or thermal energy, to modify a first plurality of ions derived from the sample. In a second example applying the thermal energy comprises applying thermal energy to a region of a spectrometer drift chamber for a selected period prior or subsequent to introducing ions into the region of the drift chamber. This second example optionally includes the features of the first example. In a third example the spectrometer drift chamber comprises an electrode for applying the RF electric field, and the thermal energy is localised within a selected distance of the electrode. This third example optionally includes the features of either or both of the first and second examples. In a fourth example applying thermal energy together with the RF electric field comprises applying the thermal energy prior to applying the RF electric field. This fourth example optionally includes the features of any of one or more of the first, second and third examples. In a fifth example the method comprises determining a temperature of a region of a spectrometer drift chamber, and only applying the thermal energy in the event that the temperature is less than a selected threshold temperature. This fifth example optionally includes the features of any of one or more of the first to fourth examples.

In a first apparatus example an ion mobility spectrometer is configured to apply one of: an RF electric field and thermal energy; to a first plurality of ions in the event that a characteristic determiner determines that ions of the sample have a first characteristic, and then to apply the RF electric field and thermal energy to a second plurality of ions in the event that the characteristic determiner determines that the first plurality of ions have a second characteristic.

In a second apparatus example, the characteristic determiner comprises a spectrometer drift chamber, and a gate for controlling the passage of ions into the drift chamber, wherein the controller is configured to operate the heater to apply thermal energy for a selected period. This second apparatus example optionally includes the features of the first apparatus example.

In a third apparatus example, the controller is configured to operate the heater to apply thermal energy in the event that the temperature is less than a selected threshold temperature. This third apparatus example optionally includes the features of the first and/or second apparatus examples.

In a fourth apparatus example an ion mobility spectrometer comprises an ion modifier configured to apply an RF electric field to ions in a region of the spectrometer; a heater configured to heat the region; and a controller configured to operate the heater to heat the region prior to operating the ion modifier to apply the RF electric field. This fourth apparatus example optionally includes the features of the first and/or second and/or third apparatus examples.

In a fifth apparatus example the heater and the ion modifier are arranged so the heater does not prevent the RF electric field from modifying ions. This fifth apparatus example optionally includes the features of one or more of any of the first to fourth apparatus examples.

It will be appreciated that in the context of the present disclosure that RF electric fields comprise any alternating electric field having frequency characteristics appropriate for applying energy to modify ions (e.g. by imparting energy to them to raise their effective temperature).

Other examples and variations will be apparent to the skilled reader in the context of the present disclosure.

Aspects of the disclosure provide computer program products, and computer readable media, such as tangible non-transitory media, storing instructions to program a processor to perform any one or more of the methods described herein. Other variations and modifications of the apparatus will be apparent to persons of skill in the art in the context of the present disclosure.

The invention claimed is:

1. An ion mobility spectrometry method comprising:
   determining whether a sample comprises ions having a first characteristic;
   in the event that it is determined that the sample comprises ions having the first characteristic, applying thermal energy together with a radio frequency, RF, electric field to parent ions so as to obtain daughter ions having a second characteristic for inferring at least one identity for the parent ions based on the first characteristic and the second characteristic, wherein applying the thermal energy comprises heating a region where the RF electric field is applied more than other regions.

2. The method of claim 1 in which determining whether the sample comprises the ions having the first characteristic comprises applying one of an RF electric field and thermal energy, to modify a first plurality of ions derived from the sample.

3. The method of claim 1 in which applying the thermal energy comprises applying thermal energy to a region of a spectrometer drift chamber for a selected period.

4. The method of claim 3 in which the spectrometer drift chamber comprises an electrode for applying the RF electric field, and the thermal energy is localised within a selected distance of the electrode.

5. The method of claim 1 in which applying thermal energy together with the RF electric field comprises applying the thermal energy prior to applying the RF electric field.

6. The method of claim 1 further comprising determining a temperature of a region of a spectrometer drift chamber, and only applying the thermal energy in the event that the temperature is less than a selected threshold temperature.

7. The method of claim 1 in which applying thermal energy comprises heating a region of a spectrometer drift chamber to a temperature that is not sufficient to modify ions without the application of an RF electric field.

8. The method of claim 1 in which applying thermal energy comprises heating a region of a spectrometer drift chamber to a temperature selected to promote ion modification by the RF electric field.

9. An ion mobility spectrometer comprising:
   a characteristic determiner for determining a characteristic of ions of a sample;
   an electrode adapted to subject the ions to an RF electric field in a region of the spectrometer;
   a heater adapted to heat the region more than other regions of the spectrometer;
   a controller configured to selectively control at least one of:
      the application of an RF voltage to the electrode; and
      the heater;
   to apply at least one of thermal energy and an RF electric field, based on the determined characteristic.

10. The ion mobility spectrometer of claim 9 in which the controller is configured to operate the electrode to apply one of: an RF electric field and thermal energy; to a first plurality of ions in the event that the characteristic determiner determines that ions of the sample have a first characteristic, and then to apply the RF electric field and thermal energy to a second plurality of ions in the event that the characteristic determiner determines that the first plurality of ions have a second characteristic.

11. The ion mobility spectrometer of claim 9 in which the characteristic determiner comprises a spectrometer drift chamber, and a gate for controlling the passage of ions into the drift chamber, wherein the controller is configured to operate the heater to apply thermal energy for a selected period.

12. The ion mobility spectrometer of claim 9 in which the controller is configured to operate the heater to apply thermal energy in the event that the temperature is less than a selected threshold temperature.

13. The ion mobility spectrometer
   of claim 9 where the controller is configured to operate the heater to heat the region prior to operating the electrode to apply the RF electric field, wherein the electrode comprises an ion modifier.

14. The ion mobility spectrometer of claim 13 comprising a drift chamber, and a detector configured to detect the passage of ions along the drift chamber, and a gate configured to control the passage of ions into the drift chamber, in which the heater is disposed in a position selected from the list consisting of: at a drift gas inlet of the drift chamber; in the drift chamber between the ion modifier and the gate; in the drift chamber between a detector and the ion modifier; and carried by a wall of the drift chamber about the ion modifier.

15. The ion mobility spectrometer of claim 13 comprising a drift chamber, wherein the ion modifier is disposed in the drift chamber and the spectrometer comprises a source of infrared radiation arranged to apply infrared radiation to the localised region in the drift chamber.

16. The ion mobility spectrometer of claim 13 in which the ion modifier comprises the heater.

17. The ion mobility spectrometer of claim 13 comprising a characteristic determiner for determining a characteristic of the ions, wherein the controller is configured not to operate the heater unless the characteristic determiner indicates the presence of ions having one of a selected set of characteristics.

18. The ion mobility spectrometer of claim 13 comprising a temperature sensor, wherein the controller is configured not to operate the heater unless the temperature is less than a selected threshold temperature.

\* \* \* \* \*